United States Patent
Duveneck et al.

(10) Patent No.: US 6,395,558 B1
(45) Date of Patent: May 28, 2002

(54) OPTICAL CHEMICAL/BIOCHEMICAL SENSOR

(75) Inventors: Gert Ludwig Duveneck, Bad Krozingen (DE); Jürg Dübendorfer, Wheaton; Rino Ernst Kunz, Steinmaur, both of (CH); Gerolf Kraus, Bad Bellingen-Bamlach (DE)

(73) Assignee: Zeptosens AG, Witterswil (CH)

(*) Notice: Subject to any disclaimer, the term of this patent is extended or adjusted under 35 U.S.C. 154(b) by 0 days.

(21) Appl. No.: 09/242,983

(22) PCT Filed: Aug. 27, 1997

(86) PCT No.: PCT/EP97/04678
§ 371 (c)(1),
(2), (4) Date: Aug. 5, 1999

(87) PCT Pub. No.: WO98/09156
PCT Pub. Date: Mar. 5, 1998

(30) Foreign Application Priority Data

Aug. 29, 1996 (CH) .............................................. 2131/96

(51) Int. Cl.⁷ .............................................. G01N 21/76
(52) U.S. Cl. ................ 436/172; 422/82.11; 422/82.05; 250/227.14; 385/12
(58) Field of Search ...................... 436/172; 422/82.11, 422/82.05; 250/227.14; 385/12

(56) References Cited

U.S. PATENT DOCUMENTS

| | | | | |
|---|---|---|---|---|
| 3,905,676 A | * | 9/1975 | Ulrich | 385/37 |
| 4,880,752 A | * | 11/1989 | Keck et al. | 435/7 |
| 4,886,341 A | * | 12/1989 | Oishi et al. | 350/162.22 |
| 5,081,012 A | * | 1/1992 | Flanagan et al. | 435/7.9 |
| 5,082,629 A | * | 1/1992 | Burgess et al. | 422/82.11 |
| 5,166,515 A | * | 11/1992 | Attridge | 250/227.25 |
| 5,195,161 A | * | 3/1993 | Adar et al. | 385/129 |
| 5,442,169 A | * | 8/1995 | Kunz | 250/227.21 |
| 5,604,829 A | * | 2/1997 | Bruesselbach | 385/37 |
| 5,623,561 A | * | 4/1997 | Hartman | 385/12 |
| 5,814,565 A | * | 9/1998 | Reichert et al. | 422/82.11 |
| 5,822,472 A | * | 10/1998 | Danielzik et al. | 385/12 |
| 5,961,924 A | * | 10/1999 | Reichert et al. | 422/82.11 |
| 6,078,705 A | * | 1/2000 | Neuschafer et al. | 385/12 |

FOREIGN PATENT DOCUMENTS

| | | |
|---|---|---|
| WO | 8607149 | 12/1986 |
| WO | 9110122 | 7/1991 |
| WO | 9219976 | 11/1992 |
| WO | 9533198 | 12/1995 |
| WO | 9635940 | 11/1996 |

OTHER PUBLICATIONS

Kunz et al. "Finite grating depth effects for integrated optical sensors with high sensitivity", Biosens. Bioelectron., 1996, v. 11 (6/7), pp. 653–667.*

* cited by examiner

Primary Examiner—Jill Warden
Assistant Examiner—Yelena G. Gakh
(74) Attorney, Agent, or Firm—Wenderoth, Lind & Ponack, L.L.P.

(57) ABSTRACT

The invention relates to a planar ATR and evanescently exited luminescence optical sensor platform, consisting of a transducer and a recognition layer, wherein changes in the effective refractive index of the recognition layer are converted into a measurable variable in accordance with the integrated-optical light pointer principle. The invention relates also to the use of the method and to the method itself using the sensor platform, for example in label-free biosensory analysis.

16 Claims, 1 Drawing Sheet

OPTICAL CHEMICAL/BIOCHEMICAL SENSOR

CROSS REFERENCE TO RELATED APPLICATION

This application is a 371 application of PCT/EP97/04678 filed Aug. 27, 1997.

BACKGROUND OF THE INVENTION

1. Field of the Invention

The invention relates to a planar optical sensor platform, consisting of a transducer and a recognition layer, wherein changes in the effective refractive index of the recognition layer are converted into a measurable variable in accordance with the integrated-optical light pointer principle. The invention relates also to the use of the method and to the method itself using the sensor platform, for example in label-free biosensory analysis.

2. Description of the Related Art

The integrated-optical light pointer principle is described in WO 92/19976. It is based on the conversion of the change in the coupling angle, for coupling a light beam into a waveguide by means of a diffraction grating, into a position-dependent change in the signal, that is to say the coupling-in position, on the transducer. By means of the embodiments described below, the condition for coupling in a light beam covering a relatively large portion of the grating, which extends substantially perpendicularly to the direction of propagation of a guided mode, is met only at a specific position of the coupling-in grating. In the event of a change in the so-called effective refractive index for the guided mode, for example as a result of the adsorption of molecules on the grating, the coupling-in position is displaced on the grating perpendicularly to the direction of propagation of the guided mode. In this connection WO92/19976 proposes devices and methods wherein at least one coupling condition is made position-dependent. The position-dependency of the coupling condition is obtained preferably by varying the waveguide thickness or the grating period in a position-dependent manner or by varying other parameters, for example the refractive indices of substrate, cover layer and waveguide film, in a position-dependent manner. Combinations of the above position-dependent variations are also of particular interest. Special preference is given to two variants proposed in WO92/19976: with a coupling-in grating of constant period by the application of a waveguiding layer having a layer thickness that changes perpendicularly to the direction of propagation of the guided mode or by variation of the grating period of the coupling grating perpendicular to the mode propagation, with the layer thickness of the waveguide being constant. Further comments relating to the calculation, dimensioning and manufacture of transducers containing such integrated-optical light pointers can be found in "Replicated chirped waveguide gratings for optical sensing applications", published in "Sensors and Actuators A 46–47" (1995), pages 482–486.

BRIEF SUMMARY OF THE INVENTION

When a light beam is guided in a waveguide, the associated electromagnetic field is not wholly restricted to the actual waveguide, but rather the field extends into the adjacent optically thinner areas (that is to say areas of a lower refractive index). This is referred to as a transversely attenuated wave. The field, which rapidly decreases in intensity as it becomes more distant from the waveguide, is referred to as an evanescent field. The depth of penetration into the medium of lower refractive index adjacent to the waveguide is in the order of magnitude of a fraction of a wavelength, which is comparable to the dimensions of relatively large biomolecules. Processes that take place outside the depth of penetration of the evanescent field are (essentially) not detected by the guided light and therefore have (essentially) no influence on a measuring signal generated as a result. That is the basis for the large number of uses of optical waveguides in sensory analysis. The proposed sensor platform is based on the change in the so-called effective refractive index in the region of the recognition layer, which is located at least partly in the evanescent field.

According to the invention, in the simplest case the planar sensor consists of a transducer and a recognition layer. The transducer again consists of a substrate (support material), optionally an intermediate layer, a waveguiding layer and optionally an adhesion-promoting layer for the immobilisation of the recognition layer. Specifically for thin waveguides where the thickness of the waveguiding layer is smaller than the wavelength of the light, the number of propagatable modes of the light field is limited to a few discrete waveguide modes.

DETAILED DESCRIPTION OF THE INVENTION

In the case of thick waveguides a large number of modes can be guided; in this case a substrate (support material) is often unnecessary, for example for thicknesses in the region of a few tenths of a millimetre and larger.

The use of one or more coupling gratings for the coupling-in and/or coupling-out of guided waves according to the prior art is described in K. Tiefenthaler, W. Lukosz, "Sensitivity of grating couplers as integrated-optical chemical sensors", J. Opt. Soc. Am. B6, 209 (1989), W. Lukosz, Ph. M. Nellen, Ch. Stamm, P. Weiss, "Output Grating Couplers on Planar Waveguides as Integrated, Optical Chemical Sensors", Sensors and Actuators B1, 585 (1990), and in T. Tamir, S. T. Peng, "Analysis and Design of Grating Couplers", Appl. Phys. 14, 235–254 (1977). The procedures described in Tiefenthaler et al and Lukosz et al. are useful for affinity sensory analysis using the direct detection method (by way of the change in refractive index) in which the shift in the coupling angle resonance, which, caused by adsorption or binding of molecules onto the surface, results from the change in refractive index, is determined.

The problem underlying the invention is to provide a miniaturisable sensor platform based on a planar optical waveguide and a recognition layer, wherein changes in the recognition layer are converted in accordance with the integrated-optical light pointer principle.

That problem is solved by a planar optical sensor platform consisting of a transducer and a recognition layer, wherein changes in the effective refractive index in the region of the recognition layer are converted into a measurable variable in accordance with the integrated-optical light pointer principle.

Figure 1:
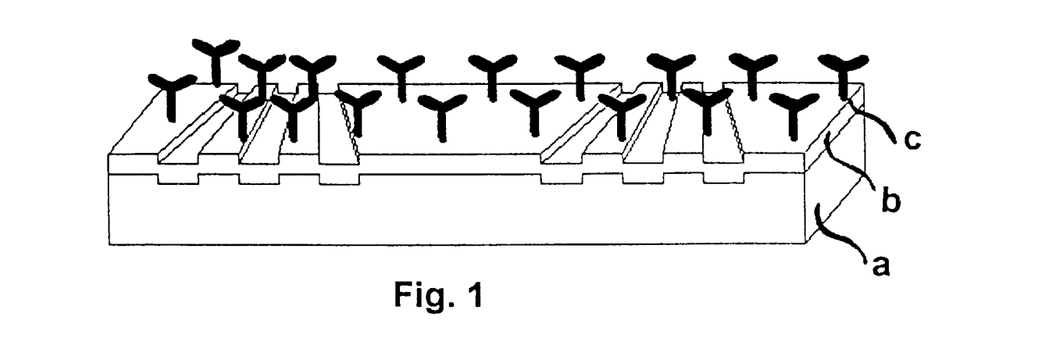
FIGS. 1 and 2 show different embodiments of planar optical sensor platforms according to the invention, comprising a support material (a), a waveguiding layer (b) and a recognition layer (c).
Figure 2:
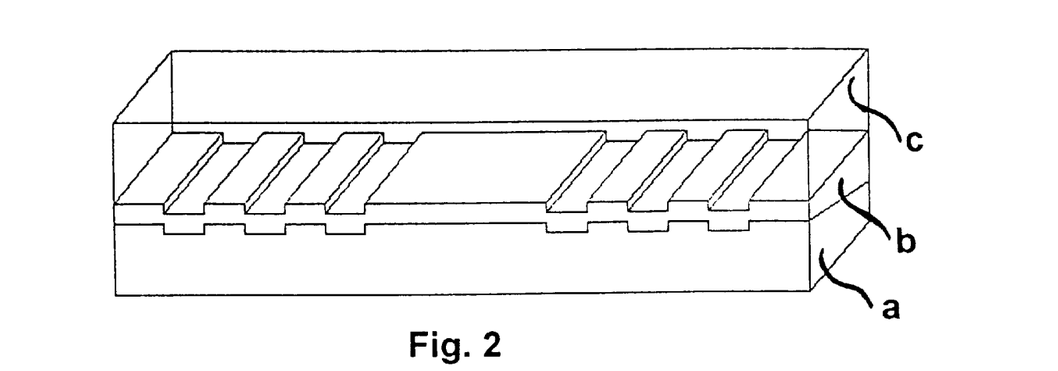

For practical reasons, preference is given to a planar optical sensor platform consisting of a preferably transparent support material (a) to which there are applied at least one thin, transparent waveguiding layer (b) and a recognition layer (c), the refractive index of the support material (a) being lower than the refractive index of the waveguiding layer (b) and the sensor platform being provided with a coupling grating for coupling in the excitation radiation, and the integrated-optical light pointer principle being realised by the waveguiding layer and the coupling-in grating.

Preferably the sensor platform has, physically separate from the first coupling grating, a second coupling grating for coupling out the wave guided in the waveguiding layer.

A planar dielectric optical sensor platform is preferred.

Preferably the coupling-in grating and the coupling-out grating (in the case of coupling-out by means of a second grating) of the sensor platform have a grating period that is non-constant perpendicular to the direction of propagation of the guided mode.

It is preferable to use a waveguiding layer of constant layer thickness. Also preferred is an embodiment using a waveguiding layer the thickness of which is smaller than the wavelength $\lambda$ of the excitation radiation and which consists of a material the refractive index of which at the wavelength of the excitation radiation is $\geq 1.8$.

In addition, it is also possible for luminescence excitation to be associated with the arrangement according to the invention. It is possible both for the luminescence radiation excited in the evanescent field and guided in the waveguide to be detected by means of coupling-out through the second grating and for that amount of luminescence that is excited in the evanescent field but emitted into the halfspace above or below the transducer to be collected and detected. Procedures and apparatuses are known from the prior art, for example from WO 95/33198.

The sensor platform according to the invention is especially suitable for a readily miniaturisable arrangement of a label-free bioaffinity sensor system. In that case the recognition layer consists of biochemical recognition elements for the analytes, immobilised on the sensor platform either directly or via a suitable adhesion-promoting layer, as described below and, for example, in WO 95/33197 and WO 95/33198.

The use as recognition layer of suitable membranes which either comprise the chemical or biochemical recognition elements or as a whole form the recognition layer and the refractive index of which changes, preferably specifically, on contact with the analyte, in liquid solution or in gases, for example as a consequence of swelling or shrinkage, provides a further advantageous embodiment of the sensor platform according to the invention.

The sensor platform according to the invention is also especially suitable as an optical ionic strength sensor. Upon simultaneous measurement of the fluorescence and the change of the effective refractive index based on the light pointer principle it is possible to determine simultaneously the pH value and the ionic strength. It is also possible to use the sensor platform as an ion-selective optical sensor, it being necessary merely to use an ionophore and not a special fluorophore or chromophore. Finally, when suitable membranes are used, for example consisting of siloxanes, the sensor platform according to the invention enables hydrocarbons to be detected in liquids or gases, especially air.

Advantageously, the sensor platform according to the invention has the potential for a high degree of miniaturisation in comparison with known refractive-index-dependent methods. Furthermore, both the light source and the detector can be integrated into the sensor platform in question or it is possible to use a sandwich consisting of the sensor platform according to the invention and a complementary excitation and detection chip, so that higher signal stability can be achieved. When used as an optical ionic strength sensor, the sensor platform according to the invention is distinguished by short response times. A further advantage is that in the case of ion-selective detection in opaque liquids, for example blood, there are no interfering signals caused by the absorption of light from the liquid and no luminescence effects. The same advantages apply to its use as a bioaffinity sensor in accordance with the light pointer principle.

The dimensioning of the planar waveguides for as efficient as possible a luminescence excitation is possible on the basis of planar waveguide theory. The following variables are involved for that purpose (W. Lukosz, "Principles and sensitivities of integrated optical and surface plasmon sensors for direct affinity sensing and immunosensing", Biosensors & Bioelectronics 6, 215–255 (1991), D. G. Hall, "Optical waveguide diffraction gratings: coupling between guided modes", in Progress in Optics XXIX, Ed. E. Wolf, Elsevier, N.Y. (1991)):

The depth of penetration of the evanescent field of a planar waveguide into the superstrate (the layer above the waveguide; recognition layer) is given by $$\Delta z_{eva} = \lambda/2\pi \cdot \frac{1}{\sqrt{N_{eff}^2 - n_{super}^2}}$$

for the effective mode refractive index $N_{eff}$, the superstrate refractive index $N_{super}$ and for the working wavelength $\lambda$, where z is the coordinate perpendicular to the waveguide surface, and x is the coordinate of the waveguide propagation. Taking into account the scaling factor f for the field strength at the waveguide surface $$f = \frac{n_{film}^2 - N_{eff}^2}{n_{film}^2 - n_{sub}^2},$$

where the refractive index of the waveguide is $n_{film}$ and of the substrate is $n_{sub}$ (support material), there is obtained an intensity curve $I_E$ of the evanescent field above the waveguide proportional to:

$$I_E \sim f \cdot e^{-2z/\Delta z_{eva}}.$$

That intensity curve of the exciting evanescent fields perpendicular to the waveguide surface determines the essential scaling magnitude for the dimensioning of the waveguide layer thickness and refractive index. For analytical uses for detecting luminescent molecules close to the waveguide layer, the distance of the molecule from the waveguide surface is to be taken into consideration in the dimensioning of the waveguide.

As regards luminescence detection, it has been put forward in WO95/33198 that for thin planar waveguides of high refractive index the evanescent backcoupling of the luminescence is an efficient method. The choice of waveguide layer thickness and refractive index have an effect both on the (calculable) excitation efficiency and on the evanescent backcoupling. In the latter case the coupling-in of the radiation components of bound molecules close to the waveguide surface competes with the coupling-in of unbound molecules from the sample volume.

Preferred sensor platforms according to the invention have wavelength parameters in the following range:

refractive index $n_{film} \geq 1.8$ at the excitation wavelength $\lambda$, layer thickness $t_{film} \leq$ excitation wavelength $\lambda$, preferably $t_{film} \leq \lambda/2$.

The thickness of the waveguiding layer is especially from 30 to 200 nm.

The modulation depth of the grating is preferably from 3 to 60 nm.

An especially advantageous arrangement of the sensor platform is obtained when the layer thickness selected is from 30 to 200 nm and at the same time the modulation depth of the grating is from 3 to 60 nm, the ratio of the modulation depth to the layer thickness being <0.5.

Those waveguides can also be such that they typically allow only the propagation of waveguide modes of a low order $m \leq 3$.

The radiation evanescently backcoupled into the waveguide is transported therein; characteristic thereof is the attenuation constant $\Gamma$ of the guided wave. Here, with a small Stokes shift, identical attenuation values for the excitation and luminescence radiation can be assumed (possible causes of waveguide attenuation are scattering losses at the interfaces of the waveguide and absorption in the waveguide layer or in the substrate (support material) or superstrate. Both for scattering and for absorption, no significant change in the attenuation as a result of the Stokes shift of typically 10–50 nm is to be expected when there are no distinct narrow absorption bands. (Such spectrally narrow-band absorption effects are to be avoided when selecting the material for the sensor platform.)

Where there is additional luminescence excitation and detection of the luminescence radiation component transported in the waveguide, that component is to be coupled-out and fed to the detection system. That is done by using for the coupling-out a second coupling grating which is physically separate from the coupling grating for coupling in the excitation radiation.

In this case an optimum value for the grating spacing B has proved to be $B=x_{1/e}$, with scope for variation in the range $B \approx (0.2-3)*x_{1/e}$ ($x_{1/e}$: 1/e length for the drop in the intensity of the guided excitation wave in the x-direction). (conversion $\Gamma[dB/cm] \rightarrow x_{1/e}[1/mm]$: $x_{1/e}=100/(\ln 10*\Gamma)$.) For larger spacings, both excitation light and guided luminescence light are strongly attenuated, resulting in a substantial reduction in the signal. The lower limit is determined not primarily by excitation and backcoupling but rather by the associated demands of the positioning of the two gratings and of the excitation beam on the coupling-in grating. Spacings of less than 100 $\mu$m are not expedient also in view of the dimensioning described below of the width of the coupling-in grating and the beam diameter of the excitation radiation on the edge of the coupling-in grating.

The angles for coupling-in and coupling-out can be set by way of the grating constants $\Lambda_1$ and $\Lambda_2$ chosen. A distinction is made between two variants:

Variant 1: coupling angle other than 0° (other than perpendicular incidence);

Variant 2: coupling angle close to 0°.

In the case of the first variant, the coupling angles are set advantageously in the range of $|\theta|>1°$ to 50° (for the value of the angle), for example by the choice of the grating constants. Smaller values should be avoided since otherwise, even with very small tolerances in the alignment or the evenness of the sensor, the light pointer will be excited in a counter direction, rendering the evaluation difficult or impossible. Larger angles up to close to 90° are possible, but if the beam path is to be realised in an advantageous manner angles far away from the sensor perpendiculars should be avoided.

In the case of the second variant, coupling-in angles of $|\theta| \leq 1°$ (for the value of the angle) are consciously sought. It is then possible to excite two light pointers which propagate in opposite directions, that is to say from the coupling-in grating towards right and left. Preferably in that case two coupling-out gratings to the left and right of the coupling-in grating are used in order to couple out the light pointers to one or more detectors. A suitable signal evaluation method, for example using differential measurement, can then be used to compensate for undesirable influences, for example instabilities of the coupling-in angle.

The So-called "Chirp" $g_\Lambda$, that is to say the change in the grating period (gradient) perpendicular to the direction of propagation of the guided mode, is governed by the size of the change in the effective refractive index to be expected in the application in question. The gradient $g_\Lambda$ is given by $$g_\Lambda(y) = \left.\frac{\delta \Lambda}{\delta y}\right|_y.$$

For linear gradients, $g_\Lambda$ is defined in accordance with the following equation:

$$\Lambda = f_\Lambda(y) = \Lambda_0 + g_\Lambda y$$

wherein $\Lambda$ is the grating period at grating height y, $\Lambda_0$ is the grating period at point y=0. A value of $g_\Lambda = 10^{-6}$ corresponds to a change in the grating period by 1 nm in the event of a change in the lateral position y by 1 mm.

For practical use, with a full range of the light pointer movement by 3 mm and an excitation wavelength of 785 nm, with a titanium dioxide waveguide (n=2.348) on a polycarbonate substrate (n=1.571), for almost perpendicular coupling-in of light, the following "Chirps" and grating periods $\Lambda_0$ are especially suitable:

variation from $n_c=1.5$ to $n_c=1.6$: $\Lambda_0=450-460$ nm; $g_\Lambda=30-40 \times 10^{-7}$ variation from $n_c=1.51$ to $n_c=1.52$: $\Lambda_0=420-460$ nm; $g_\Lambda=3-4 \times 10^{-7}$ The values are each different for the $TE_0$ and the $TM_0$ mode. Here $n_c$ is used to indicate the refractive index of the superstrate.

The dimensioning of the grating depth can be effected in accordance with the prior art (T. Tamir, S. T. Peng, "Analysis and Design of Grating Couplers", Appl. Phys. 14, 235–254 (1979); T. Tamir, "Beam and waveguide couplers", in "Integrated Optics", Ed. T. Tamir, Springer, Berlin (1979)).

The so-called "leak parameter": $\alpha$ is used herein as a characteristic: $\alpha$ describes the 1/e drop in the intensity of a guided wave in a waveguide the interface of which is provided with a coupling grating of depth $t_{grating}$. Accordingly, $1i/\alpha$ is the characteristic length for the transmission of the radiation energy from the guided wave to a freely Propagating wave and vice versa. The primary factor in the choice of the depth of the coupling-in grating is not the absolute value of the leak parameter but the matching of the leak parameter and the beam parameters of the incident light (beam diameter and divergence). The most important guidelines can be found in the publication by R. E. Kunz and L. U. Kempen, "Miniature Integrated Optical Sensors", Proc. SPIE, Vol. 2068, 69–86 (1994). Additional remarks in respect of the leak parameter that are relevant to luminescence detection have been put forward in WO95/33198 and should likewise be taken into account in the case of additional luminescence detection according to the invention.

The support material of the sensor platform is preferably transparent at the excitation and emission wavelength.

Where the support material is not transparent, the waveguiding layer is preferably separated from the support material by an intermediate layer of sufficient thickness (see below). In that case the light is preferably radiated in from the superstrate side. The support materials used can also be plastics, as described, for example, in EP-A-0 533 074.

In the case of transparent substrates the excitation and detection preferably take place from the underside of the sensor platform, that is to say through the transparent substrate.

The support material may consist, for example, of a composite system of different materials, for example a layered system on a support plate or the like. In that case only the refractive index of the material directly adjacent to the waveguiding layer needs to be lower than the refractive index of the waveguiding layer.

The sensor platform can be produced economically especially when microstructured polymers can be used as support material for the waveguide coating. In that case the detection sensitivity may be limited by the absorption of excitation light by the support material or even by the excitation of the support material's inherent luminescence, especially in the case of additional luminescence detection. The excitation of that inherent luminescence and the evanescent backcoupling take place at the waveguide/support material interface in a manner analogous to the above-described mechanisms at the waveguide/superstrate interface. Such absorption or luminescence by the support material can be avoided by an intermediate layer that has a low refractive index (that is to say a refractive index lower than that of the waveguide) and that is non-absorbent and non-luminescent, which is applied to the support material prior to the waveguide coating. An especially suitable material for the intermediate layer is $SiO_2$ or a substantially $SiO_2$-like layer having the composition $SiO_xH_yC_z$ in which small residues of hydrocarbons remain incorporated. The thickness $t_{buffer}$, of that intermediate layer should be so selected that the energy transported from the evanescent field of the guided wave to the support material side is located substantially within the intermediate layer.

A further advantage of using an intermediate layer may also be a reduction in the surface roughness of the support material. As a result, the waveguide attenuation is reduced, with positive effects on the signal/noise ratio.

Only substantially parallel light is suitable for the method according to the invention. In the context of this invention, "substantially parallel" is to be understood as meaning a divergence of less than 5°. That is to say, the light can be slightly divergent or slightly convergent. Greater divergences facilitate the alignment of the coupling-in angle, but reduce the signals obtainable, since the width of the coupling-in resonance is then considerably smaller than the divergence angle.

In the context of this invention a "planar optical sensor platform" means that the platform may be constructed in the form of a strip, a plate, a round disc or any other geometrical shape, provided that it appears planar to the naked eye. Deviations from planarity are not critical if a guided wave is capable of propagation in the waveguiding layer. The geometric shape selected may also be dependent upon the structure of the entire apparatus in which the sensor platform is installed. Arrangements that allow substantial miniaturisation are preferred.

In addition to the above-described use of organic, microstructured support materials it is also possible to use inorganic support materials, such as glasses or quartz. In comparison with polymers such materials have the advantage of having lower inherent luminescence. For the economical production of sensor platforms it may be advantageous, however, to provide those support materials with a coating of low refractive index in which the grating structure for the coupling grating is incorporated as described in EP-A-0 533 074.

The coupling gratings may also be arranged at the waveguide/superstrate interface.

Methods of producing such gratings are known. Photolithographic procedures and etching techniques are predominantly used for their production, as described, for example, in R. E. Kunz, J. Edlinger, B. J. Curtis, M. T. Gale, L. U. Kempen, H. Rudigier and H. Schütz, "Grating Couplers in Tapered Waveguides for Integrated Optical Sensing", Proc. SPIE, Vol. 2068, 313–325 (1994) and in R. E. Kunz, J. Edlinger, P. Sixt and M. T. Gale, "Replicated Chirped Waveguide Gratings for Optical Sensing Applications", Sensors and Actuators A, Vol. 47, 482–486 (1995).

The grating structure can be produced on the support material and then transferred into the waveguiding layer in which the grating structure then reproduces itself, or the grating is produced in the waveguiding layer itself.

The grating period is preferably in the range from 200 to 1000 nm.

Suitable materials for the production of the waveguiding layer are, for example, inorganic materials, especially inorganic metal oxides, such as $TiO_2$, $ZnO$, $Nb_5O_5$, $Ta_2O_5$, $HfO_2$ or $ZrO_2$. $Ta_2O_5$ and $TiO_2$ are preferred.

The present Application relates also to a method of determining the change in the effective refractive index of a recognition layer of a planar optical sensor platform, consisting of a transducer and a recognition layer, which method comprises bringing the recognition layer into contact with a sample, with changes in the effective refractive index of the recognition layer being converted into a measurable variable in accordance with the integrated-optical light pointer principle. The details and preferences given above apply analogously to the sensor platform and to the conversion of the measurable variable in accordance with the integrated-optical light pointer principle. Similarly, preferred embodiments of the method, such as the described recognition layers, for example, may result in special arrangements of the sensor platform. Further embodiments relating to the method and to the use of the method, to which this Application also relates, are described below.

In the context of this invention a "sample" is to be understood as being the entire solution to be analysed, or alternatively the gas mixture which may comprise a substance to be detected—the analyte. The detection may take place in a one-step or multi-step assay in the course of which the surface of the sensor platform is brought into contact with one or more solutions. In that process, in the case of additional luminescence detection, at least one of the solutions used comprises a luminescent substance which can be detected according to the invention. If a luminescent substance has already been adsorbed onto the waveguiding layer (b), the sample may also in this case be free of luminescent constituents.

The sample may comprise further constituents, for example pH buffers, salts, acids, bases, surface-active substances, viscosity-influencing additives or colourings. It is possible especially to use a physiological saline as solvent. If, in the case of additional luminescence detection, the luminescent component is itself liquid, the addition of a solvent can be omitted. In that case the content of luminescent substance in the sample may be up to 100%.

The sample may also be a biological medium, for example egg yolk, a body fluid or constituents thereof, especially blood, serum, plasma or urine. Furthermore it may be surface water, solutions of extracts from natural or synthetic media, such as soils or parts of plants, or liquors from biological or synthesising processes.

The sample may be used either undiluted or with added solvent.

Suitable solvents are water, aqueous buffer solutions and protein solutions, and organic solvents. Suitable organic solvents are alcohols, ketones, esters and aliphatic hydrocarbons. Water, aqueous buffers or a mixture of water with a miscible organic solvent are preferably used.

The sample may, however, also comprise constituents that are not soluble in the solvent, such as pigment particles, dispersants, and natural and synthetic oligomers or polymers. The sample is then in the form of an optically opaque dispersion or emulsion.

In the case of additional luminescence detection it is possible to use as luminescent compounds luminescent dyes having a luminescence in the wavelength range from 330 nm to 1000 nm, such as rhodamines, fluorescein derivatives, coumarin derivatives, distyryl biphenyls, stilbene derivatives, phthalocyanines, naphthalocyanines, polypyridyl/ruthenium complexes, for example tris(2,2'-bipyridyl)ruthenium chloride, tris(1,10-phenanthroline) ruthenium chloride, tris(4,7-diphenyl-1,10-phenanthroline) ruthenium chloride and polypyridyl/phenazine/ruthenium complexes, platinum/porphyrin complexes, for example octaethyl-platinum-porphyrin, long-lived europium and terbium complexes or cyanine dyes. Especially suitable for analyses in blood or serum are dyes having absorption and emission wavelengths in the range 600–900 nm. Where the sample is a solution of a plant extract, dyes having an excitation and emission spectrum in the visible range and near infrared range, with the exception of the chlorophyll absorption range (from 660 nm to 700 nm), are especially suitable.

More especially suitable are dyes, such as fluorescein derivatives, that contain functional groups by means of which they can be covalently bonded, for example fluorescein isothiocyanate.

Also very suitable are the functional fluorescent dyes commercially available from Biological Detection Systems Inc. and from Amersham, for example the mono- and bifunctional Cy5™ and Cy5.5™ dyes, which are also described, for example, in Clinical Chemistry 40 (9): 1819–1822, 1994.

The preferred luminescence, in the case of additional luminescence excitation, is fluorescence. Coherent light is preferably used for the excitation since it is thus possible to meet the resonance condition at the coupling-in grating with a high degree of efficiency. The laser light sources used for that purpose should be selected in accordance with the absorption wavelengths of the luminescent or fluorescent molecules.

Laser diodes or superluminescence diodes are of special importance because such light sources allow a high degree of miniaturisation of the detection system assigned to the sensor platform.

Very especially suitable are laser diodes which, optionally together with the detection unit, can either be integrated into the sensor platform or combined therewith to form a sandwich consisting of the sensor platform and a complementary excitation and detection chip.

The luminescent dyes used in the case of additional luminescence excitation may also be chemically bonded to polymers or to one of the binding partners in biochemical affinity systems, for example antibodies or antibody fragments, antigens, proteins, peptides, receptors or their ligands, hormones or hormone receptors, oligonucleotides, DNA strands and RNA strands, DNA or RNA analogues, binding proteins such as protein A and G, avidin or biotin, enzymes, enzyme cofactors or inhibitors, lectins or carbohydrates.

Furthermore it is also possible to use luminescence-labelled steroids, lipids and chelators. Especially for hybridisation assays with DNA strands or oligonucleotides in the case of additional luminescence excitation, intercalating luminescent dyes are also particularly suitable, especially when—like various ruthenium complexes—they exhibit an increase in luminescence when intercalated. When those luminescence-labelled compounds are brought into contact with their affinity partners immobilised on the surface of the sensor platform, their binding can readily be determined quantitatively by reference to the measured luminescence intensity. Equally, it is possible to effect a quantitative determination of the analyte by measuring the change in luminescence when the sample interacts with the luminophores, for example in the form of luminescence extinction by oxygen or luminescence enhancement resulting from conformational changes in proteins.

In the method according to the invention, the sample can be stationary when brought into contact with the waveguiding layer or it can be passed continuously over the waveguiding layer, the circulation being open or closed.

A specific embodiment of the method, in the case of additional luminescence detection, consists in immobilising the luminescent substances used for detection of the analyte directly on the surface of the waveguiding layer (b). Such a substance may be, for example, a protein-bound luminophore which can thus be excited to luminescence on the surface of the waveguiding layer. If a partner having affinity for the protein is passed over that immobilised layer, the luminescence may be changed thereby and in that way the amount of the partner having affinity can be determined. In particular, it is also possible for both partners of an affinity complex to be labelled with luminophores in order, for example, to carry out determinations of concentration on the basis of the transfer of energy between the two, for example in the form of luminescence extinction.

A further embodiment of the method comprises using as recognition layer suitable membranes which either comprise the chemical or biochemical recognition elements or as a whole form the recognition layer and the refractive index of which changes, preferably specifically, on contact with the analyte, in liquid solution or in gases, for example as a consequence of swelling or shrinkage. Here too there is the possibility of combining detection in accordance with the light pointer principle with additional luminescence detection.

Another, preferred embodiment of the method for chemical or biochemical affinity assays consists in immobilising on the surface of the sensor platform a specific binding partner as chemical or biochemical recognition element for the analyte itself or for one of the binding partners. This may be a one-step or multi-step assay in the course of which, in successive steps, one or more solutions containing specific binding partners for the recognition elements immobilised on the surface of sensor platform are passed over that surface, the analyte being bound in one of the component steps. The analyte is detected by the change in the effective refractive index of the recognition layer, it being possible in the case of additional luminescence detection to utilise the binding of luminescence-labelled participants of the affinity assay. The luminescence-labelled substances used may be any one or more binding partners of the affinity assay, as desired, or may alternatively be an analogue of the analyte provided with a luminophore. The only prerequisite is that the presence of the analyte should result selectively in a luminescence signal or selectively in a change in the luminescence signal.

The immobilisation of the recognition elements can be effected, for example, by hydrophobic adsorption or covalent bonding directly on the waveguiding layer or after chemical modification of the surface, for example by silanisation or the application of a polymer layer. In addition, in order to facilitate the immobilisation of the recognition elements, a thin intermediate layer, for example consisting of $SiO_2$, may be applied as adhesion-promoting layer directly on the waveguide. The thickness of that intermediate layer should not exceed 50 nm, and preferably should not exceed 20 nm.

Recognition elements that come into consideration are, for example, antibodies for antigens, binding proteins such as protein A and G for immunoglobulins, receptors for ligands, oligonucleotides and single strands of RNA or DNA for their complementary strands, avidin for biotin, enzymes for enzyme substrates, enzyme cofactors or inhibitors, and lectins for carbohydrates. Which of the affinity partners in question is immobilised on the surface of the sensor platform is dependent upon the architecture of the assay.

The assay itself can be either a one-step complexing process, for example a direct assay or a competitive assay, or a multi-step process, for example a sandwich assay.

In the simplest example of the direct assay consisting of a single binding step, with detection being effected by a change in the effective refractive index, the sample, which comprises the analyte in an unknown concentration, is brought into contact with the surface of the sensor platform where the analyte molecules are bound to the immobilised recognition elements. That results in a change in the effective refractive index in dependence upon the mass of the bound analyte molecules, combined with a corresponding change in the position of the light pointer. The magnitude of the signal change is in this case proportional to the amount of bound analyte molecules. In the case of additional luminescence detection the simplest case is a competitive assay. In that case the sample again comprises the analyte in an unknown concentration as well as a known amount of a compound that is similar apart from being luminescence-labelled. When the sample is brought into contact with the surface of the sensor platform, the luminescence-labelled and unlabelled molecules compete for the binding sites on their immobilised recognition elements. In that assay configuration, a maximum luminescence signal is obtained when the sample comprises no analyte. As the concentration of the substance to be detected increases, the observable luminescence signals decrease. Such a competitive assay can also be carried out on the basis of the change in the effective refractive index, in which case a mass label is used instead of a luminescence label.

In a competitive immunoassay, the recognition element immobilised on the surface of the sensor platform does not have to be the antibody but may alternatively be the antigen. Generally it is a matter of choice in a chemical or biochemical affinity assay which of the partners is immobilised.

Furthermore, in competitive assays the competition need not be restricted to binding sites on the surface of the sensor platform. For example, a known amount of an antigen can be immobilised on the surface of the sensor platform and then brought into contact with the sample which contains as analyte an unknown amount, which is to be detected, of the same antigen as well as corresponding specific antibodies. In that case the competition for binding the antibodies takes place between antigens immobilised on the surface and antigens in the solution.

The simplest example of a multi-step assay is a sandwich immunoassay in which a primary antibody is immobilised on the surface of the sensor platform. The binding of the antigen to be detected and of the secondary antibody used to complete detection to a second epitope of the antigen can be carried out either by successive contact with the antigen-containing solution and with a second solution containing the secondary antibody or after previously combining those two solutions, so that finally the part-complex, consisting of antigen and secondary antibody, is bound. In the case of the sandwich assay, the signal levels are proportional to the amount of bound analyte molecules. In the manner described herein, the detection of the analyte can be carried out both on the basis of the light pointer principle and by means of additional luminescence detection, in this case using a luminesence-labelled secondary antibody.

Affinity assays may also include further additional binding steps. In the case of sandwich immunoassays, for example, in a first step protein A can be immobilised on the surface of the sensor platform. The protein specifically binds immunoglobulins to its so-called $F_c$ portion and these then serve, for example, as primary antibodies in a subsequent sandwich assay which can be carried out as described.

There are many other forms of affinity assay, for example using the known avidin-biotin affinity system.

Examples of forms of affinity assay can be found in J. H. Rittenburg, Fundamentals of Immunoassay; in Development and Application of Immunoassay for Food Analysis, J. H. Rittenburg (Ed.), Elsevier, Essex 1990, or in P. Tijssen, Practice and Theory of Enzyme Immunoassays, R. H. Burdon, P. H. van Knippenberg (Eds), Elsevier, Amsterdam 1985.

Furthermore, it is possible for the surface of the sensor platform to be used once only or for it to be regenerated. Under suitable conditions, for example at low pH, at elevated temperature, using organic solvents or using so-called chaotropic reagents (salts), the affinity complexes can be selectively dissociated without substantially impairing the binding ability of the immobilised recognition elements. The precise conditions are greatly dependent upon the individual affinity system.

A further important form of application of the method is based firstly on the limitation of the generation and detection of signals to the evanescent field of the waveguide, and secondly on the reversibility of the affinity complex formation as an equilibrium process: using suitable flow rates in a flow system, the binding or desorption, i.e. dissociation, of bound affinity partners in the evanescent field can be followed in real time. The method is therefore suitable in kinetic studies for the determination of different association or dissociation constants and also in displacement assays.

The detection can be carried out using known methods. Photodiodes, photocells, photomultipliers, CCD cameras and detector arrays, for example CCD rows, are suitable. For recording signals in accordance with the light pointer principle there are especially suitable position-sensitive and more especially laterally resolved detection methods, for example using CCD rows or arrays. It is also possible to use in the detection beam path further optical elements, such as mirrors, prisms, lenses, Fresnel lenses and graded index lenses, microlenses and microlens arrays for the purpose of projection onto the detectors. In the case of additional luminescence detection there are suitable for the selection of the emission wavelength known elements such as filters, prisms, monochromators, dichroic mirrors and diffraction gratings.

The method can be carried out in a simple manner by radiating in the excitation light in "continuous wave" (cw) operation, that is to say that excitation is effected with a light intensity that is constant over time.

Furthermore, pulse excitation may be employed, in which case the excitation light is radiated in the form of a timed pulse having a pulse length of, for example, from one picosecond to 100 seconds and the changes in the position of the light pointer or in the luminescence are detected in a time-resolved manner—in the case of short pulse lengths—or at intervals ranging from seconds to minutes. That method is especially advantageous when, for example, the rate of formation of a bond is to be followed analytically or, in the case of additional luminescence detection, a reduction in the luminescence signal as a consequence of photochemical bleaching is to be prevented by using short exposure times. Furthermore, in the case of additional luminescence detection, the use of suitably short pulse lengths and suitable time resolution of the detection enable scattered light, Raman emission and short-lived luminescence of any undesired luminescent constituents of the sample and of the sensor material which may be present to be distinguished from luminescence of the labelling molecule (which in this case is as long-lived as possible) by detecting the emission of the analyte only after the short-lived radiation has decayed. In addition, time-resolved luminescence detection after pulsed excitation, and, likewise, modulated excitation and detection, allow the investigation of the influence of the binding of the analyte on molecular luminescence decay behaviour. The molecular luminescence decay time can be used, alongside the specific analyte recognition by the immobilised recognition elements and the physical limitation of the generation of signals to the evanescent field of the waveguide, as a further selectivity criterion.

In the case of additional luminescence detection, the method can also be carried out by radiating in the excitation light in intensity-modulated manner, at one or more frequencies, and detecting the resulting phase shift and modulation of the luminescence of the sample.

The present invention relates also to the use of the method according to the invention in the quantitative determination of analytes in chemical or biochemical affinity assays with known affinity partners and assay architectures. In case of detection based on the light pointer principle, the analyte concentration is determined from the extent of the change in position of the light pointer. In the case of additional luminescence detection, the quantitative detection of the analyte can be carried out by detecting the emission of luminescence-labelled binding partners or by detecting changes in the luminescence characteristics of immobilised luminescence-labelled affinity partners caused by interaction with the analyte.

Since the generation and detection of signals are limited to the chemical or biochemical recognition surface on the waveguide, and interfering signals from the medium are distinct, the binding of substances to the immobilised recognition element can be followed in real time. The use of the method according to the invention for affinity screening or for displacement assays, especially for pharmaceutical product development, by means of direct determination of association and dissociation rates in a flow system having suitable flow rates, is therefore likewise possible.

The invention relates also to the use of the method in the quantitative determination of antibodies or antigens.

The invention relates likewise to the use of the method according to the invention in the quantitative determination of receptors or ligands, oligonucleotides, DNA or RNA strands, DNA or RNA analogues, enzymes, enzyme substrates, enzyme cofactors or inhibitors, lectins and carbohydrates.

The invention relates also to the use of the method according to the invention in the determination of pH and ionic strength and in the selective, quantitative determination of ions, especially in optically opaque fluids, in accordance with the light pointer principle.

The invention relates also to the use of the method according to the invention in the determination of hydrocarbons in liquids or gases in accordance with the light pointer principle.

The invention relates also, in the case of additional luminescence detection, to the use of the method according to the invention in the selective quantitative determination of constituents, especially luminescent constituents, in optically opaque fluids.

Optically opaque fluids can be, for example, biological fluids, such as egg yolk or body fluids such as blood, serum, plasma or urine, but may also be samples from environmental analysis, for example surface water, dissolved soil extracts or dissolved plant extracts. Reaction solutions such as are obtained, for example, in chemical production, especially dye solutions or reaction solutions of optical brighteners, also come into consideration. Also suitable are all types of dispersions and preparations, such as are used, for example, in the textile industry, provided that, in the case of additional luminescence detection, they contain one or more luminescent components.

The invention will be explained in greater detail below with reference to an example embodiment. The concentration M represents moles per litre.

EXAMPLE

Optical system

The light source used is a helium-neon laser ($\lambda$=632.8 nm, TM$_0$-mode, Uniphase, Manteca, USA), set using a projection system to a beam spot having a diameter in the sensor plane of 0.4 mm perpendicular to the lines of the coupling grating and 3 mm parallel to the grating lines.

Motorised adjusting units are used to set the coupling-in angle and to position the beam spot relative to the grating edge.

Linearly polarised light having TE or TM orientation, as desired, can be coupled in by means of rotatable polarising elements.

On the upper side of the sensor platform there is arranged a flow cell which is sealed with respect to the sensor by O-rings; the sample volume of this cell is approximately 20 $\mu$l. Different solutions can be introduced into the cell by way of injection pumps and switch-over valves.

The detector used for detecting the position of the light pointer is a two-dimensional CCD camera (Sony XC-77CE) with 756×581 (horizontal×vertical) active pixels, pixel area 11 $\mu$m×11 $\mu$m.

Sensor Platform

The support material used is polycarbonate which has been microstructured with two gratings for coupling-in and coupling-out as follows:

coupling-in grating with period $\Lambda_C$=356 nm, grating depth $h_g$=5 nm, Chirp $g_A$=8.57×10$^{-7}$.

coupling-out grating with period $\Lambda_0$=504.4 nm, grating depth $h_g$=5 nm, Chirp $g_A$=1.71×10$^{-6}$.

The arrangement of the grating on the sensor corresponds to the following geometric sizes: grating spacing A=400 μm, grating width (perpendicular to lines) $B_1$=$B_2$=800 μm, grating height (parallel to lines) 2.8 mm, with sensor platform dimensions: 12.5×25 mm$^2$.

On the polycarbonate support material (n=1.581 at 632.8 nm) there is a high-refractive-index waveguiding layer of TiO$_2$ having a refractive index $n_{film}$=2.389 at λ=632.8 nm and layer thickness $t_{film}$=154.5 nm.

Detection of Immunoglobulin

Solutions Used:
1) buffer solution, consisting of 1/3 phosphate buffer (0.041 M Na$_2$HPO$_4$+0.028M KH$_2$PO$_4$), 0.151M NaCl, 200 mg/l of sodium azide, 50 ml of methanol, made up to 1 litre with distilled water;
2) solution for immobilising protein A (Sigma Chemicals): 1 mg of protein A in 1 ml of distilled water;
3) rinsing solution, is also used for determining the base signal and for saturating residual binding sites (after immobilisation of protein A, see below): buffer solution 1) +1 mg/ml of bovine serum albumin (BSA, Sigma Chemicals);
4) sample solutions, rabbit immunoglobulin (rabbit-IgG, Sigma Chemicals) concentration 10$^{-8}$ M in buffer solution 1 with 1 mg/ml of BSA;
5) regenerating solution: glycine buffer, pH 3.4.

Application of the Biochemical Recognition Layer of Protein A

The optical sensor platform is incubated for 2 ours with the solution for immobilising protein A. Then the chip is washed with rinsing solution 3). In order to saturate any free adsorption sites still present, after washing the sensor platform is incubated for a further one hour in the rinsing solution which contains 1 mg/ml of BSA.

Measuring Operation/experimental Procedure:

During the entire procedure a flow of 0.25 ml/min is passed over the active sensor surface.

The procedure consists of the following individual steps:

Step 1: washing for 7 minutes with rinsing solution 3), recording of the base signal.

Step 2: supplying sample solution 4) for 18 minutes

Step 3: washing with rinsing solution 3) for 5 minutes

Step 4: supplying regeneration solution 5) for 5 minutes

Step 5: washing with rinsing solution 3) for 5 minutes.

The signal coupled out by way of the second grating is measured during the entire procedure.

Carrying out the procedure with the sensor platform coated with protein A as recognition element results in the following light pointer positions, expressed in pixel positions (px) of the CCD camera and converted into changes in the effective layer thickness $\Delta h_f$ (see in this connection R. E. Kunz, G. Duveneck, M. Ehrat, "Sensing pads for hybrid and monolithic integrated optical immunosensors", Proceedings SPIE, Vol. 2331, 2–17 (1994)) and determined at the end of the individual steps:

Step 1: y=273.6 px; $\Delta h_f$=0 (base line)
Step 2: y=291.2 px; $\Delta h_f$=1650 pm
Step 3: y=291.2 px; $\Delta h_f$=1650 pm
Step 4: y=270.0 px; $\Delta h_f$=−340 pm
Step 5: y=270.4 px; $\Delta h_f$=−290 pm The measuring accuracy in this case is approximately 1 px. The reduction in the base line after regeneration indicates that under the conditions employed a portion of the protein A recognition layer has also been removed.

Measurement of the Ionic Strength and the pH Value:

Preparation of the pH-sensitive membrane

N,N-Dimethylacrylamide and tert-butylacrylamide in a ratio of (1:1) are placed in an ampoule and dissolved in dimethyl sulfoxide so that a 30% solution is obtained. After the addition and dissolution of α,α'-azoisobutyronitrile and 4-acryloylaminofluorescein (content 1% in the end product) the ampoule is repeatedly frozen, evacuated and gassed with nitrogen in order to remove oxygen. The polymerisation is carried out for 48 hours in a water bath at 60°. A transparent, highly viscous yellow mass is obtained which, with stirring and if necessary heating, is dissolved in twice the amount of methanol (based on the amount of dimethyl sulfoxide used). The solution is added dropwise with vigorous stirring to 20 times the amount of distilled water or diethyl ether, the resulting polymer being precipitated in the form of yellow flocks which rapidly agglomerate. The polymer is filtered, dried at 100° for 24 hours, again dissolved in methanol and precipitated in distilled water or diethyl ether. After separation from the mother liquor the product is dried at 1000 for 48 hours. The resulting brittle yellow solid is very hygroscopic. The copolymer composition is tested by FT-IR-measurement, and the dye concentration by UV-spectroscopic measurement in the absorption maximum of the dye (pure dye: 442 nm, copolymerised dye: 454 nm).

The transducer is coated by spin-coating (500 revolutions per minute) using a solution of the polymer (50 mg/ml) in methanol. Under those conditions there are obtained membrane thicknesses of about 1 μm, which far exceeds the depth of penetration of the evanescent field.

4 different phosphate-citrate buffers are used in the test:

Solution 1: pH 6.7, ionic strength I=0.1M
Solution 2: pH 7.9, l=0.1M
Solution 3: pH 6.7, l=0.3M
Solution 4: pH 7.9, l=0.3M When the various solutions are supplied to the coated sensor platform the following light pointer positions, expressed in pixel positions (px) of the CCD camera, are obtained:

Solution 1: y=912 px; $\Delta n_c$=6×10$^{-3}$
Solution 2: y=864 px; $\Delta n_c$=0×10$^{-3}$ (base line)
Solution 3: y=1212 px; $\Delta n_c$=45×10$^{-3}$
Solution 4: y=1188 px; $\Delta n_c$=42×10$^{-3}$ The measuring accuracy is about 5 px; the response time of the sensor (about 90% of the total signal change) is less than one minute.

What is claimed is:

1. A planar optical sensor platform, comprising a support material (a), and at least one thin waveguiding layer (b), the refractive index of the support material (a) being lower than the refractive index of the waveguiding layer (b), and the sensor platform being provided with a coupling grating for coupling in radiation, characterized in that (1) the coupling grating has a structure which is produced on the support material and reproduced in the waveguiding layer, or the coupling grating has a structure which is produced in the waveguiding layer, (2) a recognition layer (c) is located on the waveguiding layer, and (3) said coupling grating has a grating period that is non-constant perpendicular to the direction of the mode propagation, or (4) said coupling grating has a constant grating period and the layer thickness of the waveguiding layer changes perpendicularly to the direction of propagation of the guided mode.

2. A platform according to claim 1, wherein the support material (a) is transparent.

3. A platform according to claim 1, which has, physically separated from the coupling-in grating, a second coupling grating for coupling out the wave guided in the waveguiding layer.

4. A platform according to claim 3, wherein the coupling-out grating has a grating period that is non-constant perpendicular to the direction of propagation of the guided mode.

5. A platform according to claim 1, wherein the thickness of the waveguiding layer (b) is from 30 to 200 nm.

6. A platform according to claim 3, which has, physically separated from the coupling-in grating, a further coupling grating for coupling out the wave guided in the waveguiding layer, the gratings being located to the right and the left of the coupling-in grating.

7. A platform according to claim 1, wherein the recognition layer contains recognition elements, which are immobilized by hydrophobic absorption or covalent bonding directly on the surface of the waveguiding layer, which is unmodified or chemically modified.

8. A platform according to claim 7, wherein the recognition elements are specific chemical or biochemical binding partners for an analyte.

9. A platform according to claim 8, wherein the recognition elements are selected from the group consisting of antibodies for antigens, binding proteins A or G for immunoglobulins, receptors for ligands, oligonucleotides, and single strands of RNA or DNA for their complementary strands, avidins for biotin, enzymes for enzyme substrates, enzyme cofactors or inhibitors, and lectins for carbohydrates.

10. A platform according to claim 1, wherein the recognition layer consists of a membrane, or a membrane which contains chemical or biochemical recognition elements.

11. A method for an optical determination of an analyte which comprises contacting a recognition layer of the planar optical sensor platform according to claim 1 with a sample, coupling in through the grating light from a light source, and measuring the change of the effective refractive index in the region of a recognition layer by recording the position of light points with a position sensitive detection method.

12. A method according to claim 11, wherein CCD rows or arrays are used for the detection of light points.

13. A method according to claim 11, wherein in addition luminescence radiation, which is guided in the waveguide, is coupled out by a second grating provided in the platform, or that amount of luminescence radiation that is excited in the evanescent field but emitted into the halfspace above or below the platform is fed to a determination system.

14. A method according to claim 11, wherein the sample is a body fluid or constituents thereof, surface water, a soil or plant extract or a liquor from a biological or synthesizing process.

15. A method according to claim 13 for the simultaneous determination of pH and ionic strength.

16. A method according to claim 11, wherein coupling-in of light occurs at an angle between −1° and +1° with respect to the normal of the sensor platform, so that two waves propogate in opposite directions towards right and left of the coupling-in grating.

* * * * *